United States Patent [19]

Warriner

[11] Patent Number: Plant 5,895

[45] Date of Patent: Mar. 10, 1987

[54] ROSE PLANT JACTAN

[75] Inventor: William A. Warriner, Tustin, Calif.

[73] Assignee: Jackson & Perkins Company, Medford, Oreg.

[21] Appl. No.: 771,848

[22] Filed: Sep. 3, 1985

[51] Int. Cl.[4] ..... A01H 5/00

[52] U.S. Cl. ..... Plt./3

[58] Field of Search ..... Plt./3

*Primary Examiner*—Robert E. Bagwill

*Attorney, Agent, or Firm*—Manford R. Haxton

[57] ABSTRACT

A hybrid rose variety having unusual golden tan flower color in the bud and fresh open flower stage coupled with its vigorous climbing habit and its heavy and continuous flower production.

1 Drawing Figure

This present invention relates to a new and distinct variety of rose plant of the climber class which was originated by crossing an unnamed variety with the variety Royal Sunset, U.S. Plant Pat. No. 2,072.

The primary objective of this breeding was to produce a new rose variety of the climber class with vigor and an unusual golden orange to tan color. This objective was substantially achieved along with other desirable improvements as evidenced by the following unique combination of characteristics which are outstanding in the new variety and which distinguish it from its parents as well as from all other varieties of which I am aware:

1. A unique golden tan color of the buds and the fresh open flowers;
2. The continuous and heavy production of flowers; and
3. Vigorous climbing growth habit.

Asexual reproduction of this new variety by budding, as performed at Wasco, Calif. shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Royal Sunset, U.S. Plant Pat. No. 2,072.

Classification:

*Botanical.*—Rosa hybrid.

*Commercial.*—Climber.

FLOWER

Observations made from specimens grown in a greenhouse at Irvine, Calif. in June.

Blooming habit: Continuous.

Bud:

*Size.*—1½" when petals start to unfurl.

*Form.*—Long, pointed ovoid.

*Color.*—When sepals first divide, Greyed-Orange Group 163A with streaks of Greyed Orange 17A to B; when half blown, upper side of petals Grey-Orange Group 163B-C with a Yellow half moon at the base (Yellow group 12A-B); lower side of petals, Grey-Orange Group 163B-C with a Yellow half moon at the base (Yellow group 12A-B).

*Sepals.*—Color: Green group 138A. Three appendaged sepals lightly appendaged. Two unappendaged sepals hairy edge.

*Receptacle.*—Color: Green 138B. Shape: Funnel. Size: Small. Surface: Lightly hairy.

*Peduncle.*—Length: Short. Surface: Glandular. Color: Medium green. Strength: Bending.

Open bloom:

*Size.*—Large. Average open size 4½".

*Borne.*—Several together.

*Stems.*—Medium, strong and arching.

*Form.*—When first open, high center. Permanence: Retains its form to the end.

*Petalage.*—Number of petals under normal conditions: 25.

*Color.*—Center of flower: Upper side of petals, Greyed Yellow Group 163 B to C; reverse side of petals, Greyed Yellow Group 163 B to C. Base of petals, Yellow Group 12 A-B. Major color: Greyed Yellow 161C.

*Variegations.*—None.

*Discoloration.*—General tonality at end of first day: None. Third day; Lightens to Greyed Yellow 161 C to D.

*Fragrance:*—Moderate.

Petals:

*Texture.*—Thick.

*Shape.*—Deltoid.

*Form.*—Tips slightly recurved.

*Arrangement.*—Imbricated. Petaloids in center, None.

*Persistence.*—Drop off cleanly.

*Lastingness.*—On the plant, long. As cut flower, long.

Reproduction parts:

*Anthers.*—Medium, many. Color: Yellow. Arrangement: Regular around styles.

*Filaments.*—Color: Yellow.

*Pollen.*—Gold Yellow.

*Styles.*—Color: Red.

*Stigmas.*—Color: Greenish white.

PLANT

Form: Climber.

Growth: Vigorous.

Foliage: Number of leaflets on normal mid-stem leaves: 5–7.

*Size.*—Medium.

*Quantity.*—Normal.

*Color.*—New foliage: Reddish. Old foliage: Green 137A.

Leaflets:

*Shape.*—Elliptic pointed.

*Texture.*—Leathery.

*Edge.*—Serrated.

*Serration.*—Single, small.

*Petiole.* —Rachis: Color: Reddish. Underside: Rough with many prickles.

*Stipules.*—Long, bearded.

*Disease resistance.*—Moderately resistant to mildew, under normal growing conditions at Irvine, Calif.

Wood:

*New wood.*—Color: Reddish. Bark: Smooth.

*Old Wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks, few. On laterals, many.

*Color.*—Brown.

I claim:

1. A new and distinct variety of rose plant of the climber class, substantially as herein shown and described, characterized particularly as to novelty by the unique combination of its unusual golden tan flower color in the bud and fresh open flower stage coupled with its vigorous climbing habit and its heavy and continuous flower production.

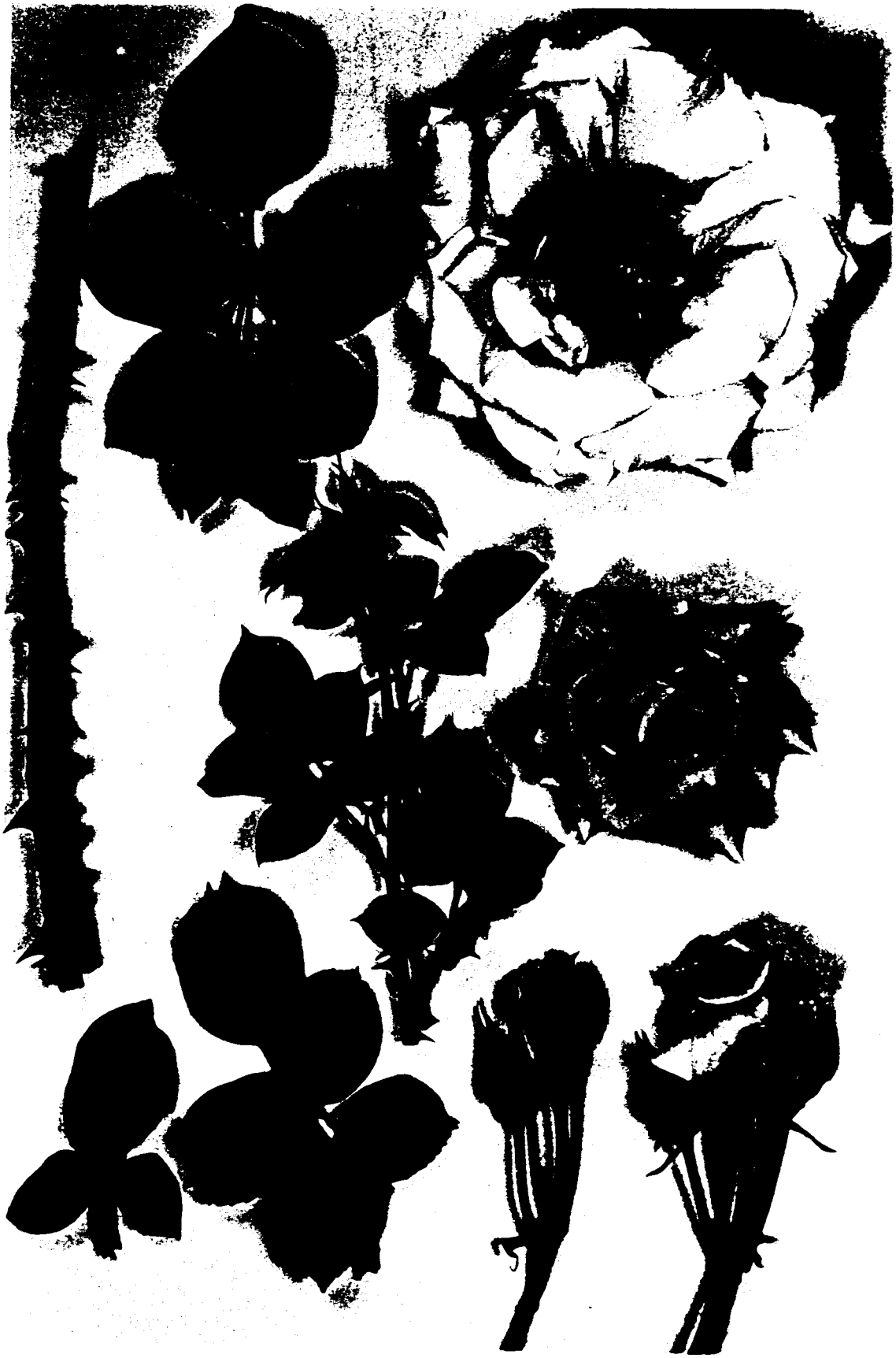

* * * * *